United States Patent [19]

Delrue

[11] Patent Number: 5,100,679
[45] Date of Patent: Mar. 31, 1992

[54] METHOD OF MAKING A MODIFIED PROTEINACEOUS PRODUCT AND COMPOSITION THEREOF

[75] Inventor: Rita M. Delrue, Bergen op Zoom, Netherlands

[73] Assignee: Cargill B.V., Bergen op Zoom, Netherlands

[21] Appl. No.: 592,268

[22] Filed: Oct. 3, 1990

[51] Int. Cl.⁵ ............................................. A23J 3/14
[52] U.S. Cl. ...................................... 426/44; 426/46; 426/50; 426/634
[58] Field of Search ................... 426/46, 50, 44, 634, 426/583

[56] References Cited

U.S. PATENT DOCUMENTS

| | | | |
|---|---|---|---|
| 3,632,346 | 1/1972 | Sherba | 99/98 |
| 3,640,723 | 2/1972 | Uhlig et al. | 99/9 |
| 3,642,490 | 2/1972 | Hawley et al. | 99/17 |
| 3,713,843 | 1/1973 | Pour-el et al. | 99/79 |
| 3,853,839 | 12/1974 | Magnino et al. | 260/123.5 |
| 3,876,806 | 4/1975 | Hempenius et al. | 426/46 |
| 3,912,822 | 10/1975 | Yokotsuka et al. | 426/44 |
| 3,917,851 | 11/1975 | Arnaud et al. | 426/46 |
| 3,941,890 | 3/1976 | Drachenberg et al. | 426/46 |
| 3,966,992 | 6/1976 | Banks et al. | 426/583 |
| 3,974,294 | 8/1976 | Schwille et al. | 426/32 |
| 4,100,024 | 7/1978 | Adler-Nissen | 195/29 |
| 4,100,151 | 7/1978 | Adler Nissen | 260/112 G |
| 4,216,235 | 8/1980 | Dasek et al. | 426/46 |
| 4,376,127 | 3/1983 | Lunde | 426/46 |
| 4,378,376 | 3/1983 | Wagner et al. | 426/41 |
| 4,478,854 | 10/1984 | Adler-Nissen et al. | 426/12 |
| 4,478,939 | 10/1984 | Adler-Nissen et al. | 435/200 |
| 4,478,940 | 10/1984 | Adler-Nissen et al. | 435/209 |
| 4,482,574 | 11/1984 | Lee | 426/7 |
| 4,483,874 | 11/1984 | Olsen | 426/44 |
| 4,490,406 | 12/1984 | Ferrero et al. | 426/634 |
| 4,512,973 | 4/1985 | Dennis et al. | 424/94 |
| 4,642,236 | 2/1987 | Friend et al. | 426/44 |
| 4,678,673 | 7/1987 | Marshall et al. | 426/46 |
| 4,882,180 | 11/1989 | Takao et al. | 426/46 |
| 4,929,558 | 5/1990 | Emura et al. | 435/252.5 |

FOREIGN PATENT DOCUMENTS 1247929 1/1989 Canada .
1153693 6/1989 Japan .

OTHER PUBLICATIONS

M. G. Van Oort, R. J. Hamer and E. A. Slager, *Recent Advances of Research in Antinutritional Factors in Legume Seeds,* Published by Pudoc in Wageningen, Netherlands, 110-113 (1989).
M. G. Van Oort, R. M. Hamer and M. Tolman, *Detection of Antigenticity Soy Proteins by Immunoblotting.*
WPI No. 88-167947/24, U.S. Pat. No. 4,748,025 to Bachmann et al.
WPI No. 89-216488/30, JP 1153693.
WPI No. 83-59211K/25, EP 81262 to Olivieri et al.
WPI No. 72-62707T/39, JP 72038178.
WPI No. 72-55769T/35, U.S. Pat. No. 3,682,646.
Abstract of NL 6617705A.
WPI No. 82-71269E/34, U.S. Pat. No. 4,477,472.
WPI No. 73-42610U/30, JP 73024262.
WPI No. 83-801103/43, U.S. Pat. No. 4,409,256.
WPI No. 76-96704X/52, GB 1459422.
WPI No. 86-031786/05, JP 60251850.
WPI No. 87-334855/47, JP 1502316.
Abstract of EP 334057A (1989).
Abstract of U.S. Pat. No. 4,234,620.
WPI No. 85-247291/40, JP 60164441.
WPI No. 86-073759/11, JP 61025460.
WPI No. 81-16068D/10, GB Pat. 1585456 to Croon.
Abstract of U.S. Pat. No. 4,944,952 to Kobayashi et a., *Official Gazette*, p. 2519, Jul. 31, 1990.

*Primary Examiner*—Donald E. Czaja
*Assistant Examiner*—Helen Pratt
*Attorney, Agent, or Firm*—Fitch, Even, Tabin & Flannery

[57] ABSTRACT

A process and composition thereof for making a proteinaceous product which comprises preparing an aqueous slurry of soy protein; treating the slurry by adjusting the pH to about 3.5 to about 6 and adding a viscosity reducing agent selected from the group consisting of a proteolytic enzyme and carbohydrase enzyme and an antioxidant, or mixtures thereof to form a pretreated slurry; heating the pretreated slurry, to a temperature not greater than 155° C. such that the pretreated slurry does not contain a substantial amount of proteinaceous antinutritional factors and antigenicity factors; treating the pretreated slurry with a hydrolyzing agent from a source of alpha-galactosidase; and drying the proteinaceous material to form a soy product.

50 Claims, No Drawings

METHOD OF MAKING A MODIFIED PROTEINACEOUS PRODUCT AND COMPOSITION THEREOF

BACKGROUND OF THE INVENTION

Field of the Invention

This invention relates generally to the treatment of vegetable sources of nutrients, and more particularly to the treatment of vegetable proteins and carbohydrates in order to improve the palatability and digestibility thereof, to an extent that permits such foodstuffs to be utilized as nutrients for human and animal consumption.

The latent nutritional values present in many vegetables, particularly the oilseed vegetables such as soybeans and other legumes and cottonseeds, is well known. Utilization of these nutrient sources has been severely hampered by the presence in these vegetable nutrients of naturally occurring substances that interfere with their digestibility and palatability.

A particular field of use where it would be desirable to utilize vegetable nutrients is in the preparation of milk substitutes for the replacement of mothers' milk, particularly in the feeding of young farm animals such as calves and pigs. Milk replacers for these young animals has become an important sector of the animal feed business. Understandably, dried milk products such as skim milk, whey and casein have been considered to be the most desirable nutrient source for milk replacers. However, the unpredictable and relatively high price of milk derived nutritive source has stimulated a interest in lower cost alternative nutrient sources provided that they are capable of producing equivalent growth rates to that produced by milk derived substitutes in the young animals to which they are fed.

The principal deficiencies of vegetable nutrient sources is their typical beany flavor and their poor digestibility. The beany flavor, particularly when used as an animal feed can be overcome by cooking or toasting. However, the poor digestibility of vegetable nutrients, such as soy protein is caused by the presence of oligosaccharide sugars, antinutritional factors as trypsin inhibitor and proteins that show antigenicity.

These sugars are antinutritional factors, because they cause flatulence. This flatulence results in discomfort, diarrhea, loss of appetite and poor growth, all of which has prevented the wide-scale use of vegetable nutrients as milk replacers for human consumption.

The proteins with antigenicity are believed to interfere with or slow down the growth rate of young animals. The antigenic factors are generally associated with the presence of glycinin, betaconglycinin, lectin and urease that occur naturally in vegetable nutrients such as soy beans and cottonseed. In young animals, the presence of these substances results in diarrhea, poor growth and even mortality.

Vegetable nutrients especially soy products also typically contain factors which inhibit the natural digestive action of the trypsin enzyme in the intestine. These trypsin inhibiting factors may be reduced to below 1.0 mg inhibited trypsin per gram product by heat treatment, for example by heating to a temperature above 85° C. for 6 minutes.

The deficiencies of vegetable nutrient are well known and many attempts have been made to provide treatment processes to improve their palatability and digestibility. U.S. Pat. No. 4,512,973 discloses inactivation of soybean trypsin inhibitors with a trypsin enzyme derived from starfish in combination with a supplementary proteolytic enzyme.

Several methods for hydrolyzing the flatulence producing sugars have also been suggested. The flatulence producing sugars are those sugars, principally the alpha oligosaccharide, stachyose, raffinose and saccharose, that are not digested in the digestive tract and enter the lower intestine intact where they are anaerobically fermented which results in the production of carbon dioxide, hydrogen and methane. U.S. Pat. Nos. 4,483,874, 4,376,127, 4,216,235 and 3,632,346 describe various enzymatic treatments which are indicated to result in hydrolysis or degradation of the flatulence producing sugars to digestible mono- and di-saccharide sugars.

U.S. Pat. No. 4,485,874 discloses the preparation of a milk substitute from crude vegetable protein and carbohydrate sources using an enzyme having multiple carbohydrase activities. The addition of other enzymes such as amylases and/or proteases to the carbohydrase enzyme is suggested.

In the treatment process described in U.S. Pat. No. 4,483874, a crude source of vegetable protein and carbohydrate, for example, full fat or defatted beans or cottonseed, soy flour or meal, is cooked to inactivate trypsin inhibiting factors. The cooked material is slurried in water and contacted with the enzyme at an elevated temperature that is below that at which the enzyme is inactivated, at or slightly below 50° C., the resulting product may be fed directly as a substitute milk source or may be augmented with additional sources of fat, protein and carbohydrate depending on the nutrient content of the starting raw material. Typically, augmentation is required to obtain the nutrient level of mother's milk.

It has been determined that although, the end products obtained by the process of U.S. Pat. No. 4,483,874 are satisfactory fluid milk substitutes, the disclosed process is not susceptible to scale up for commercial production, particularly where it is desirable, or it typically is where an animal milk replacer is the desired end product, to provide a dried product which is purchased and reconstituted by the end user.

Vegetable nutrient sources, for example, soybean meal or flour, form highly rigid slurries when mixed with water which are difficult to handle on a commercial scale.

Accordingly, it is necessary to utilize highly dilute slurries having relatively low solids content, generally below 15 percent by weight and typically below 10 percent by weight in order to permit handling of the slurry without the necessity of special pumps, increased electrical costs, etc. Typically, soybean flour slurries having 20 percent by weight solids content show a viscosity increase during storage from about 2,000 to about 7,000 cps at 40° C.

Low solids content slurries, while desirable from the standpoint of handleability during processing, are cost inefficient when a dried product is desired. For example, the cost of spray drying a 10 percent solids slurry obtained from the procedure of the '874 Patent may be as much as 3.9 times the cost of spray drying a 30 percent solids slurry per unit weight of product.

Thus, it is highly desirable to develop an efficient and effective process for treating vegetable protein and carbohydrates in order to improve palatability and digestion for animal and human consumption. Additionally, it is also highly desirable to develop a milk substitute which is cost efficient and easy to use.

SUMMARY OF THE INVENTION

It would be desirable to provide an improvement in the process of U.S. Pat. No. 4,483,874 to provide improved processing efficiencies. It has been discovered that such improvement may be realized by pretreatment of the soy slurry to cause partial degradation of the non-starch polysaccharides which result in a significant reduction in the slurry viscosity before the heat treatment and during further processing. This permits the solids content of the slurry to be increased which reduces drying costs and results in overall process economy.

In a preferred embodiment, the slurry of a vegetable source of protein and carbohydrate containing in excess of about 21 percent dry solids by weight is prepared. Such a slurry typically has a viscosity at 40° C. of 4,000 cps. If left untreated, the viscosity of such slurry will increase to over 7,000 cps within 5 hours. The slurry is pretreated with a viscosity reducing agent that reacts with the non-starch polysaccharides and proteins. The time, temperature and concentration of the viscosity reducing agent are controlled as to provide a slurry viscosity of less than about 2,000 cps at a dry solids content of about 21.5 percent by weight. The pretreated slurry is then heat treated to inactivate the protein antinutritional factors.

The heat treated slurry is then subjected to a hydrolyzing agent. The hydrolyzing agent is alpha-galactosidase. The primary function of which is to hydrolyze the flatulent producing sugars, principally raffinose, stachyose and saccharose to digestible monosaccharides. In a preferred embodiment, the hydrolyzing agent also includes the use of carbohydrase enzyme for further degradation of non-starch polysaccharides and results in further lowering of the slurry viscosity. A protease type of enzyme can also be added to the hydrolyzing agent with or without the carbohydrase enzyme.

After enzyme digestion, the digestibility and palatability of the vegetable protein and carbohydrates are improved to the extent that they may be directly used as a nutrient source. Most desirably, however, the slurry is dried, typically by spray drying, to provide a free flowing powder or agglomerated product which is reconstituted by the end user and mixed with additional nutrients, typically milk derived protein, sugar and fat to provide a milk substitute that is nutritionally equivalent to mother's milk.

DETAILED DESCRIPTION OF THE PREFERRED EMBODIMENTS

The treatment of the present invention is described in connection with the use of comminuted vegetable protein and carbohydrates, more specifically, defatted soy flour and soy meal. The defatted soy contains less than 1.2% oil and about 50% protein. Alternatively, defatted rapeseed meal or cottonseed and germ meal may be utilized. Note, all weight percents herein were measured on dry solids.

To obtain a soy product that has substantially no antinutritional factors and has good dispersibility, an aqueous slurry is first prepared. The slurry is prepared by admixing soy flour, water and an acid so that the pH of the slurry is between about 3.5 and 6. The slurry is then pretreated with a viscosity reducing agent selected from the group consisting of a carbohydrase enzyme and an antioxidant. Furthermore, the viscosity reducing agent can be a mixture of the two or three components of a carbohydrase enzyme with an antioxidant and/or an amino acid.

The pretreated slurry is then heated by injection of live steam followed by high shear mixing of the product. The conditions are chosen as such that in the soy slurry the proteinaceous antinutritional factors are greatly reduced or inactivated. Other heating conditions can be employed so long as the antinutritional factors are substantially eliminated. The pretreated slurry is cooled, then treated with a hydrolyzing agent from the source of an alpha-galactosidase which can be combined with carbohydrase or protease individually, or all three components can be used together. Preferably, the hydrolyzing agent is a mixture of alpha-galactosidase and a carbohydrase, and more preferably, the hydrolyzing agent is a mixture of alpha-galactosidase, carbohydrase and a protease. This proteinaceous material is dried to form a protein product.

To prepare the aqueous slurry, soy flour is preferably used. The soy flour is prepared from white or toasted soy flakes. Coarse or fine flakes can be used. These ground flakes can be ground so the flakes can pass through about a 70 to about a 1000 micron sieve, see U.S. Pat. Nos. 4,478,940 and 4,478,856, which are incorporated herein by reference. More preferably, the ground flakes can pass through a 100 to 500 micron sieve. The soy flour is mixed with water at a temperature of 30° C. to 60° C., preferably 45° C., to form a slurrying between about 15 to about 35 weight percent dry solids, preferably about 20 to about 30 weight percent, more preferably about 24 to about 28 weight percent dry solids. The pH of the slurry is adjusted between about 3.5 to about 6, and preferably, about 4.0 to about 5.0. To adjust the pH the following acids are preferred: hydrochloric acid, phosphoric acid and organic acids which could include, but are not limited to, citric acid, ascorbic acid and maleic acid. A mixture of hydrochloric acid with organic acids could also be used, with the combination of hydrochloric acid and citric acid being preferred.

In accordance with the present invention, the highly viscous slurry is pretreated by contact with a viscosity reducing agent, which reacts mainly with the non-starch polysaccharide and proteins, and thereby lowers the viscosity of the slurry. This viscosity reducing agent is selected from the group consisting of a carbohydrase enzyme, an antioxidant, and mixtures thereof. The viscosity reducing agent could contain a protease enzyme and/or an amino acid.

The carbohydrase enzyme can be derived from an enzyme complex containing several enzyme activities which degrade the non-starch polysaccharides, most preferred activities are cellulase, hemicellulase, pectinase, xylanase, invertase, beta-glucanase, cellobiase, arabinase, and the like. The carbohydrase enzyme is usually derived from fungi (multinuclear filaments), preferably *Trichoderma reseii* and *Asperoillus niger*. As a viscosity reducing agent, the carbohydrase enzyme is used in an amount of about 0.02 to about 1.5 weight percent, preferably about 0.1 to about 0.8 weight percent. If the enzyme is expressed in enzyme activity, the enzyme employed has an activity of 120 FBG units/ml.

Any antioxidant can be used, so long as it is diluted for food chemistry for either animal or human consumption. A sulfite-type antioxidant is preferred, particularly sodium meta-bisulfite. The antioxidant is used in an amount of about 0.05 to about 1.2 weight percent, preferably about 0.1 to about 0.6 weight percent. If sodium meta-bisulfite or any other sulfite type antioxidant is used, a neutralizer is added before drying the slurry. Hydrogen peroxide is the preferred neutralizer.

The amino acid preferably is cysteine and is used in an amount of about 200 to about 800 ppm. Preferably, the viscosity reducing agent is a carbohydrase mixture, where the mixture contains a carbohydrase enzyme and either or both a protease, an antioxidant and an amino acid. The components are within the ranges prescribed above.

Even most preferred, the carbohydrase enzyme is mixed with an antioxidant. Most preferred, the viscosity reducing agent is a mixture of carbohydrase enzyme with sodium-meta bisulfite as the antioxidant.

The viscosity reducing agent is added to the slurry at a temperature of about 30° C. to about 60° C., preferably about 40° C. to 45° C. The reaction time for the viscosity reducing agent is generally about two hours, but is dependent upon the amount of soy flour used and the desired reduction of the viscosity. The viscosity of the slurry is about 800 to about 4000 cps, preferably lower than about 2000 cps, where viscosity is measured at 40° C. using a Brookfield Spindle Viscosimeter. The pretreatment lowers the viscosity of the slurry such that, even after the heating step, the pretreated slurry is not so high in viscosity that further processing is difficult.

The pretreated slurry is heated to above 85° C. Generally, the pretreated slurry is heated in a jetcooker line, which is composed of live steam injection followed by a high speed mixer, although any mechanical means may be used for this heating step, provided the temperature of the preheated slurry is above 85° C., but not higher than 155° C. When using a jet cooker line, direct steam, about 8 to about 13.5 Bar, is injected to bring the temperature above 85° C. After the addition of steam, there is a through high speed mixing step which guarantees a sufficient mixing of the steam/slurry. The pretreated slurry can be heated to about 100° C. to about 135° C. with a retention time of about 2 to 12 minutes, preferably to about 105° C. to about 120° C. with a retention time of about 4 to about 7 minutes. The heated, pretreated slurry is then cooled to about 70° C. to about 95° C. in a flashcooler using a vacuum, preferably about 80° C. to 90° C. and then cooled to a second temperature of about 30° C. to about 55° C., preferably about 45° C. to about 50° C.

Generally, the slurry is first pumped into a jet cooker where it is heated above 115° C. and then is passed through a holding tube to give residence time of at least about 50 seconds to about 480 seconds, preferably about 80 to about 300 seconds. By heating the pretreated slurry, unwanted proteinaceous antinutritional factors are inactivated substantially.

Next, the pretreated slurry is cooled to a second temperature through a flashcooler, and then cooled in a cooler. It is also possible to use a plate and/or tube cooker. It should be noted that, if a jetcooker is used without a mixing step, higher temperatures are generally employed, but care must be taken to avoid denaturing the proteinaceous material. Denaturing of the proteins will result in low nutritional value of the end product. Benefit can be obtained by using lower temperatures in that there is less chance of denaturing proteins, and by using lower temperatures, the color of the final proteinaceous product is lighter.

The cooled, pretreated slurry is further treated with a hydrolyzing agent. The hydrolyzing agent is alpha-galactosidase, but could also contain a carbohydrase enzyme and/or a protease enzyme. Preferably, the hydrolyzing agent is a mixture of carbohydrase enzyme and alpha-galactosidase. More preferably, the hydrolyzing agent is a mixture of alpha-galactosidase, carbohydrase and protease enzymes. The standard reaction time is about 4 hours, but can be varied according to the dry solids content of the slurry and the amount of enzymes used. Note, the pretreated slurry should be cooled as stated herein so that when the enzyme mixture is added, the enzymes are not inactivated due to the temperature of the pretreated slurry being too high. The resulting proteinaceous matter has a viscosity of about 500 to about 3500 cps, preferably about 500 to 2500 cps at 50° C., measured by a Spindle Brookfield Viscosimeter.

The carbohydrase enzyme is preferably a multienzyme complex which degrades non-starch polysaccharides and contains enzyme activities such as cellulase, hemicellulase, pentosanase, beta-glucanese, xylanase, cellobiase, pectinase, invertase and arabinase. These enzymes are produced by fungi. The preferred carbohydrase is VISCOZYME 120L, which ca be purchased at NOVO-Nordisk, ROHAMENT 7069 from Rohm, or Cellulase CE from Alko.

VISCOXYME 120L is a mixture of enzymes produced from a fungi of the *Aspergillus* strain, preferably *Aspergillus niger*. The carbohydrate enzyme can be produced from other strains of fungi such as *Aspergillus oryzae, Trichoderma* strain, preferably *Trichoderma longibrachiatum*, formerly *Trichoderma reseii; Penicillium* strain, preferably *Penicillium emersonii, Penicillium funicullosum* and mixtures thereof.

The activity of carbohydrase is expressed in FBG units/mol, where FBG is fungal beta glucanase unit. The activity is at least 120 FBG units/ml. The multienzyme complex should contain at least the following enzyme activities: cellulase 150–800, xylanase 140–800, pectinase 50–10,000, hemicellulase 100–600, pentosanse 300–1000, beta-glucanase 1500–7000, cellobiase 1–10, all in micromol. product/minute/gram substrate units.

the protease can be from fungal, bacterial and plant extracts and mixtures thereof, or more specifically, fungi from the *Aspergillus* strain, preferably *Aspergillus oryzae; Bacillus* strain, preferably *Bacillus lichenformis* and *Bacillus subtilus*; and from plant extracts such as papain. A bacterial protease is preferably used with an activity of 0.5AU/g, where AU is Anson units. The more preferred protease is produced from *Bacillus subtilus*. NEUTRASE 0.5L is the most preferred protease which can be purchased at NOVO Nordisk. Preferably, a bacterial protease is used with an activity of 0.5 AU/-gram. The protease is employed to hydrolyze the proteins and to increase the solubility of the final proteinaceous product.

The alpha-galactosidase is selected from a group fungal or bacterial alpha-galactosidase or mixtures thereof. Alpha-galactosidase is made by NOVO Nordisk. Alpha-galactosidase can be produced from fungi from the *Aspergillus* strain, preferably *Aspergillus niger* and *Aspergillus oryzae*; the *Monascus* strain, preferably *Monascus pilosus*; and from bacteria from the *Bacillus* stain, preferably *Bacillus stearothermphilus*. The alpha-galactosidase is preferably of fungal origin (*Aspergillus* strain) with an activity of 250 GAL unit/gram (GALU is galactosidase units). Mot preferred is fungal alpha-galactosidase from an *Aspergillus niger* strain with a minimum activity of 250 GALU/gram. The alpha-galactosidase catalyses the hydrolyeses of several sugars such as raffinose, stachyose, and saccharose. When treating the slurry with the enzyme mixture, the temperature is maintained from about 35° C. to about 60° C., preferably about 40° C. to about 45° C. Optionally, the pH of the enzyme/slurry mixture is adjusted to maintain a pH of about 4.0 to about 5.5, preferably about 4.5 to abut 5.0, by adding hydrochloric acid, phosphoric acid citric acid, sodium carbonate or sodium hydroxide.

When the hydrolyzing agent is just alpha-galactosidase (250 GALU/gram), it is used in an amount of about 0.2 to about 1.3, preferably about 0.4 to about 1.0, more preferably about 0.5 to about 0.8 weight percent.. If the alpha-galactosidase has an activity that is higher or lower than 250 GALU/gram, the amount used is adjusted. If the dosage is expressed in GALU/gram dry proteinaceous material for the enzyme treatment, the alpha-galactosidase (250 GALU/gram) is used in an amount of about 0.50 GALU to about 3.25 GALU, preferably about 1.0 GALU to about 2.5 GALU, more preferable 1.25 GALU to about 2.0 GALU.

When the hydrolyzing agent contains, in addition to alpha-galactosidase, a carbohydrase enzyme with an activity of 120 FBG/ml, the carbohydrase enzyme is used in an amount of about 0.1 to about 1.0 weight percent, preferably about 0.2 to about 0.85 weight percent. If the carbohydrase enzyme has a lower or higher activity than 120 FBG/ml, the dosage is corrected. If the dosage of the carbohydrase enzymes is expressed in FBG units per gram proteinaceous material for the enzyme treatment, the carbohydrase enzyme is used in an amount of 0.1 to about 1.0 FBG, preferably about 0.2 to about 0.85 FBG units per gram dry product. When the hydrolyzing agent contains a carbohydrase enzyme with an activity of 120 FBG/ml and the alpha-galactosidase has an activity of 250 GALU/gram, the mixture added to the pretreated slurry per gram dry proteinaceous material contains about 1.0 GALU to about 2.0 GALU and 0.15 FBG units to about 1.0 FBG units per gram dry product.

The hydrolyzing agent that contains the protease in addition to the alpha-galactosidase and carbohydrase enzymes is used in an amount of about 0.5 to about 2.4 weight percent, preferably about 0.65 to about 2.25 weight percent, whereby the alpha-galactosidase enzyme has an activity of 250 GALU/gram, the carbohydrase enzyme has an activity of 120 FBG/ml and the protease has an activity of 0.5 AU/gram.

Calculated on the activity of the enzymes, the enzyme mixture contains about 0.0005 to about 0.005 AU protease activity, about 0.1 to about 1.0 FBG carbohydrase activity and about 0.35 to about 2.5 GALU/gram alpha-galactosidase activity to be added to one gram dry product. More preferably, the mixture to one gram of product contains about 0.00125 to about 0.004 AU protease activity, about 0.2 to about 0.85 FBG carbohydrase enzyme activity, and about 1.0 to about 2.5 GALU/gram alpha-galactosidase activity per gram dry product. Most preferably, the enzyme mixture is about 0.5 percent carbohydrase, 0.2 percent protease and about 0.6 percent alpha-galactosidase based upon the weight percent of the slurry.

Another measure that can be taken to remove the soluble sugars in the pretreated slurry is to decant the pretreated slurry. The problem with decanting is that it sometimes reduces the yield of the end product. Therefore, decanting can be done in addition after the enzyme treatment, if so desired. By decanting it is meant that continuous solids are separated from suspensions. The liquid phase can pass through a centrifuge to recover the solids.

After forming the proteinaceous matter, it is advisable to pasteurize the matter to make sure that microbial activity is minimized. To pasteurize the proteinaceous matter, the slurry is pumped through a heat exchanger to raise a temperature of about 85° C. for 10 to 20 seconds. If desired, the slurry can be corrected with sodium hydroxide or sodium carbonate or calcium hydroxide to obtain a pH of about 5.0 to about 6.5. The proteinaceous matter is dried by flash drying or spray drying to thereby form a proteinaceous product, wherein spray drying is the preferred technique. When drying the proteinaceous matter, the hydrolyzing agent is a mixture of alpha galactosidase and carbohydrase enzymes. Most preferred, the hydrolyzing agent also contains a protease. Generally, the proteinaceous matter is dried such that the proteinaceous product contains about 3 to about 11 percent moisture, preferably, about 4 to about 8 percent moisture, most preferably about 4 to about 6 percent moisture based upon the weight of the final proteinaceous product. Additionally, if so desired, but not necessary, amino acids can be added before or after drying the proteinaceous product to further upgrade the product nutritionally, with lysine and/or methionine being preferred.

The proteinaceous product comprises: about 48 to about 54 percent protein, about 10 to about 22 percent simple sugars (measured by HPLC), which include about 4 to about 9 percent glucose and galactose and about 3 to about 6 percent fructose. The levels of saccharose, stachyose and raffinose are individually lower than 0.5 percent. The dried product is a free-flowing product and contains substantially no antinutritional factors and antigenicity factors as determined with the described method. The level of trypsin inhibitor is lower than 1.0 (mg trypsin inhibited per gram of product). The proteinaceous product has good dispersibility characteristics. The proteinaceous product is easily mixed with water and there are little if no undissolved clumps in the water. Additionally, the proteinaceous product, when employed as a calf milk replacement product, has little or no separation problems, even after 24 hours. The proteinaceous product is mixed with water at below about 30 percent of the product.

The proteinaceous product can be used in many different applications, of which could include calf milk replacement, pet food, pig starter, fish feed and in food for human consumption. The composition of milk replacer varies from product to product, corresponding to the needs of the young animal. In very general terms, the milk replacer contains protein, carbohydrate and fat. The proteinaceous product herein can be used as the protein source in the milk replacement product.

The proteinaceous product is a replacement for standard or normal milk replacers up to about 75 weight percent replacement. More specifically, such a milk replacer contains about 5 to about 30 weight percent proteinaceous product, about 30 to about 50 weight percent whey protein products and about 5 to about 20 weight percent skim milk; more preferably, about 10 to about 25 weight percent proteinaceous product, about 35 to about 45 weight percent whey protein products and about 10 to about 15 weight percent skim milk; most preferred is about 19 weight percent proteinaceous product, about 42 weight percent whey protein products and about 11 weight percent skim milk, with the balance constituting about 20 weight percent fat and the rest being minerals and emulsifiers, where the weight percent is based on the final milk replacer composition. Because the hydrolyzing agent increases the emulsifying capacity of the resulting proteinaceous product, it is possible to add less emulsifier in the substitute milk replacer and, if so desired, either add more minerals or even increase the amount of proteinaceous product used therein. Preferably, the milk replacer also contains about 1 to about 10 weight percent starch or pregelatinized starch, preferably about 4 to about 6 percent based on the weight of the calf milk replacement product.

The proteinaceous product can be used in other applications, such as pet food. When employing the proteinaceous product in pet food, it is desirable to make the proteinaceous product such that, when treating the pretreated slurry with the hydrolyzing agent, the mixture comprises the carbohydrase enzyme and alpha-galactosidase. This hydrolyzing agent is preferred since, if the protease is added, the resulting pet food will show reduced texture. In applications for pet food, it is also advised to decant the slurry before the final drying step. When decanted, the amount of lower or reducing sugars in the proteinaceous product will be reduced to levels lower than 8 percent.

The proteinaceous product can also be used in foods for human consumption, of which such foods could include the following: baby food, protein rich beverages, meat imitations, sausages, imitation cheese and the like. The amount of proteinaceous product added to the food product is dependent upon the food product formulation. There are generally no constraints to the amount employed.

The following examples are not to limit or narrow the invention herein, but are for illustrative purposes only.

EXAMPLES

EXAMPLE 1

Example 1 (i):

The following Table 1(i) specifies the ingredients in milk, a milk base product and the proteinaceous product herein, with two formulations of milk base and two for soy base.

TABLE 1(i)

| (ALL IN WT %) | MILK | MILK REPLACER MILK BASE C1 | C2 | SOY BASE A1 | A2 |
|---|---|---|---|---|---|
| Protein | 28 | 20–22 | 20–22 | 20–22 | 20–22 |
| Simple sugars | 38 | 40 | 40 | 35 | 35 |
| Fat | 30 | 20 | 20 | 20 | 20 |
| Skim milk | NA | 40 | 50 | 30 | 25 |
| Whey products | NA | 30 | 20 | 34 | 35 |
| Soy conc. | NA | 0 | 0 | 6 | 10 |
| Fat | NA | 20 | 20 | 20 | 20 |
| Emulsifier | NA | 3.5 | 3.5 | 3.5 | 3.5 |
| Nutrients | NA | 5 | 5 | 5 | 5 |
| Starch | NA | 5 | 5 | 5 | 5 |

Example 1 (ii):

The following Table 1(ii) illustrates the physical and chemical properties of the proteinaceous product herein, A–$A_2$, and compares it to that of soy bean concentrate (SBC) and soy bean meal (SBM), where SBC has been treated to remove some carbohydrate and other anti-nutritional factors and is slightly less digestible than milk protein. Milk protein is 92 to 95 percent digestible and SBC is 80 to 85 percent digestible. The problem with use of SBC is that use is cost prohibitive. Soy bean meal is an inexpensive source of protein, but unmodified, it has relatively poor protein digestibility of 63 to 67 percent along with anti-nutritional and antigenic factors that limit its use. Note that the proteinaceous product herein, A and A1 were treated with different enzymatically treatment steps. A was treated with the viscosity reducing agent, a carbohydrase enzyme, and with the hydrolyzing agent containing carbohydrase and protease; where A1 and A2 were pretreated with viscosity reducing agent carbohydrase, but the hydrolyzing agent in the final treatment step also contained an alpha-galactosidase.

As can be seen from Table 1(ii), the raffinose and stachyose were almost completely degraded in samples $A_1$ and $A_2$.

TABLE 1(ii)

Physical and Chemical Properties of Soy Products

| % of dry solids | SBC | SBM | A | A1 | A2 |
|---|---|---|---|---|---|
| Protein | 66.3 | 52 | 52 | 52 | 52 |
| Ash | 6 | 6.9 | 7.2 | 7.2 | 7.2 |
| Fat | 0.5 | 2.5 | 0.3 | 0.3 | 0.3 |
| Fructose | — | 0.2 | 1.4 | 3 | 4.5 |
| Galactose | — | 0.3 | 1.0 | 2 | 2.1 |
| Glucose | — | 0.7 | 3.4 | 5.3 | 6.2 |
| Saccharose | — | 8.9 | 1.5 | <0.2 | <0.2 |
| Stachyose | — | 6.1 | 3.6 | <0.2 | <0.2 |
| Raffinose | — | 1.1 | 0.8 | <0.2 | <0.2 |
| Fiber | 4.5 | 3.6 | 3.1 | 3 | 3 |
| Water | 9 | 10 | 6 | 6 | 6 |
| TIF | 2.5 | 9.5 | 0.4 | 0.3 | 0.3 |
| Antigenicity | + | ++ | — | — | — |

EXAMPLE 2

Example 2 (i):

An eight week study was conducted where calves were fed a milk placement product that was made from the proteinaceous product herein. This eight week veal calf milk replacer study was designed to compare the proteinaceous product to other milk replacement products and to other milk products. The following milk replacers were employed:

TABLE 2(i)

| | MILK REPLACERS | | |
|---|---|---|---|
| | A | C1 | C2 |
| Protein | 50.00 | 84.00 | 64.00 |
| Lysine | 3.10 | 5.20 | 4.00 |
| Methionine | 0.75 | 2.10 | 0.90 |
| Methionine & Cystine | 1.47 | 3.10 | 1.85 |
| Crude Fiber | 3.00 | 0.20 | 4.50 | where A = proteinaceous product made according to the invention
C1 = comparative soy isolate as NOURISH and is supplied/produced by Loders Croklaan
C2 = comparative soy concentrate, SOYCOMILL, is supplied/produced by P.T.I. (Protein Technology International)

Example 2 (ii):

The ingredient and nutrient composition of the calf milk replacement is shown in Table 2(ii). Protein levels in all milk formulations were obtained primarily through the use of skim milk and whey protein products. All three soy sources in Comparative 1 (C1), Comparative 2 (C2) and the invention herein (A) were added to the mixture and substituted 34 to 35 weight percent of the protein in the milk replacer. In the last soy source, another example of the invention herein, A1, the proteinaceous product substituted 50 percent of the protein in the milk replacer. Lysine and methionine were added to the flour soy treatments contained in all the soy formulations to obtain the same level of lysine and methionine contained in milk formulations. As can be see from Table 2(ii) the iron concentration in the calf milk replacement seems to be affected by the level of soy product used rather than the source of the soy product.

TABLE 2(ii)

| MILK REPLACERS | | | | | |
|---|---|---|---|---|---|
| Ingredients | all milk | C1 | C2 | A | A1 |
| 8/50 Fat concentration | 33.50 | 33.75 | 33.75 | 33.75 | 33.75 |
| Whey 11.8% | 12.35 | 29.98 | 26.63 | 21.89 | 26.037 |
| Skim milk | 35.00 | 18.50 | 19.00 | 20.75 | 10.50 |
| Pregel starch | 5.00 | 5.00 | 5.00 | 5.00 | 5.00 |
| Liquid Fat | 3.00 | 3.00 | 3.00 | 3.00 | 3.00 |
| Premix, vitamins & minerals | 1.00 | 1.00 | 1.00 | 1.00 | 1.00 |
| Neo-terra 100/50 antibiotics | 0.40 | 0.40 | 0.40 | 0.40 | 0.40 |
| L-lysine | — | 0.11 | 0.133 | 0.12 | 0.175 |
| DL-Methionine | — | 0.01 | 0.08 | 0.09 | 0.138 |
| Whey prot. conc. 34 | 9.75 | — | — | — | — |
| Proteinaceous Product | — | — | — | 14.00 | 20.00 |
| NOURISH | — | 8.25 | — | — | — |
| SOYCOMILL | — | — | 11.0 | — | — |
| TOTAL | 100.00 | 100.00 | 100.00 | 100.00 | 100.00 |
| Nutrients | Formulated | | | | |
| Protein | 20.00 | 20.00 | 20.01 | 20.02 | 20.00 |
| Fat | 20.04 | 20.04 | 20.06 | 20.04 | 20.07 |
| Lysine | 1.67 | 1.67 | 1.68 | 1.66 | 1.66 |
| Methionine | 0.63 | 0.63 | 0.63 | 0.64 | 0.65 |
| Cystine | 0.37 | 0.36 | 0.34 | 0.46 | 0.51 |
| Meth. + Cyst. | 1.00 | 0.99 | 0.97 | 1.10 | 1.16 |
| | Analyzed | | | | |
| Protein | 20.00 | 21.00 | 20.80 | 20.70 | 20.90 |
| Calcium | 0.68 | 0.62 | 0.62 | 0.62 | 0.58 |
| Phosphorus | 0.45 | 0.51 | 0.51 | 0.47 | 0.47 |
| Fat | 22.40 | 21.90 | 21.80 | 21.90 | 21.30 |
| Moisture | 7.56 | 6.97 | 7.02 | 8.11 | 7.66 |
| Iron, ppm | 52.50 | 66.10 | 64.80 | 69.60 | 88.50 |
| Lysine | 1.75 | 1.61 | 1.57 | 1.53 | 1.41 |

Example 2 (iii):

Mixability is another criteria which is of importance. As can be seen in Table 2 (iii) below, there are little or no lumps in A or A1, while some degree of undissolved lumps were observed for the other treatments. Furthermore, residue remaining for A and A1 was considerably less than for treatment of all milk, C1 and C2. Mixability was measured in the following manner: calf mil replacement (.91 kg) products were placed in feeding pails and 2.5 kg of water were added to each pail and stirred with a wire brush for 10 seconds. Another 2.5 kg of water was added to each pail and the mixture was stirred for an additional 10 seconds. After sitting at room temperature for 2 minutes, the calf milk replacement products were strained through two layers of cheesecloth and insoluble particles/lumps were retained and weighed.

TABLE 2(iii)

| Mixability of Experimental Milk Replacers | | | | | |
|---|---|---|---|---|---|
| | All Milk | C1 | C2 | A | A1 |
| Visual Lumping | much on top | some | much throughout | little/none | little/none |
| Residue after mixing, grams as-is | 15.9 | 5.3 | 23.8 | 1.8 | 1.1 |
| Residue after mixing, grams dry matter | 7.7 | 3.5 | 17.9 | .4 | .3 |
| Residue after mixing, % of dry matter | .9 | .4 | 2.1 | .05 | .04 |

Example 2 (iv):

Stability of the product after mixing is another important criteria for a calf milk replacement product, see Table 2 (iv). Generally, milk replacers, especially those made from soy products, tend to separate over time. Separation could be observed in as little as 30 minutes, but was difficult to quantify for all milk replacers. The final test was the amount of mixing necessary to re-suspend the milk replacer, which was measured in seconds. Upon mixing, all milk, A1 and A2 went rapidly into complete suspension, while C1 and C2 were more difficult to re-suspend. The milk replacers which were the most difficult to re-suspend were C1 and C2. In trials for A1 and A2, no measurable residual matter was observed in the bottom of the containers.

TABLE 2(iv)

| Time | All milk | C1 | C2 | A1 | A2 |
|---|---|---|---|---|---|
| 30 min. | little or no separation | same | same | same | same |
| 2 hr. | bottom 20% darker | bottom 25% darker | bottom 33% darker | top 25% clear | no separation |
| 8 hr. | same as 2 hr | bottom 29% darker | same as 2 hr. | same as 2 hr | middle 10% clear |
| 24 hr. | same as 2 hr | same as 8 hr | same as 2 hr | same as 2 hr | same as 8 hr |
| mixing time to resuspend sec. | 3 | 10 | 9 | 3 | 2 |

Example 2 (v):

The performance of the calves overall during the study is shown in Table 2 (v). Calves at 3 to 5 days of age, weighting approximately 45 Kg., were placed on the study. C1 and C2 were not significantly different than the proteinaceous treatment, but better than all milk. All of the soy sources had less scouring than the all milk treatment, and A1 had the least amount of scouring.

TABLE 2(v)

| CALVES' PERFORMANCE | | | |
|---|---|---|---|
| ITEM | ALL MILK | A | A1 |
| Body Weight | | | |
| Initial, kg | 46.0 | 46.0 | 45.4 |
| Final, kg | 82.8 | 84.5 | 82.3 |
| Daily Gain, g | 656a | 690a | 658a |
| Intake g/day | | | |

TABLE 2(v)-continued

| | CALVES' PERFORMANCE | | |
|---|---|---|---|
| ITEM | ALL MILK | A | A1 |
| CMR-1 | 1155a | 1209a | 1177a |
| Protein-2 | 231 | 250 | 246 |
| Lysine-2 | 20.2 | 18.5 | 16.3 |
| Conversion | | | |
| CMR:gain-1 | 1.76a | 1.75a | 1.81a |
| Protein:gain | 0.352 | 0.362 | 0.378 |
| Lysine:gain | .031 | .027 | .025 |
| Health | | | |
| Scour Score-3 | 1.83a | 1.37b | 1.21c |
| Scour Days/calf | 2.9a | 1.7a | 1.2a | a, b, c - means in the same row with different superscripts are different (P, .05).
1- CMR = Calf Milk Replacer, air dry basis.
2- Protein and lysine values were calculated using analyzed values (Table 2(i)). Statistical analysis was not conducted on protein or lysine calculations.
3- Scours scoured on a scale of 1 = normal, firm stool to 4 = severe scours.

Summary of Example 2

This study demonstrates that performance equivalent to, or better than, an all milk formulation can be obtained when high quality soy sources do replace more than 35 weight percent of the protein in a milk replacer containing 20 weight percent protein. Addition of the soy sources tended to improved gut health, as evidenced by the improvement in scour or decrease in scourging. Increasing the level of proteinaceous product up to 50 percent of total protein, not total diet, improved scores, mixability and stability of the calf milk replacement product.

Example 3 Antigenicity Test

Calf milk replacers from Example 2 were evaluated to determine the antigenicity of each mixture, along with the soy products, prior to their use in the calf milk replacement product. To measure the antigenicity and trypsin inhibitor, the following assays were used: (1) Trypsin inhibitor assay- M. G. Van Oort, R. J. Hamer, E. A. Slager, *Recent Advances of Research in Antinutritional Factors in Legume Seeds*, Published by Pudoc in Wageningen, Netherlands, p. 110–113 (1989) and (2) Antigenicity Test- M. G. Van Oort, R. J. Hamer, M. Tolman, *Detection of Antigenicity Soy Proteins by Immunoblotting*. The results of the antigenicity test are as follows:

| Calf milk replacer | Antigenicity |
|---|---|
| NOURISH 3000 C1 (35%) | − |
| SOYCOMILL C2 (35%) | +/− |
| A (35%) | − |
| A1 (50%) | − |

| Antigenicity of the soy products used in the test: | |
|---|---|
| Product | Antigenicity |
| NOURISH 3000 (Isolate) | − |
| SOYCOMILL (Concentrate) | ++ |
| EMS (Enzyme modified soy flour) | − | where − is: no antigenicity.
where +/− is: trace of antigenicity.
where ++ is: antigenicity is positive.

As can be seen from Example 3, there is substantially no antigenicity in A or A1.

Example 4

This example can be used to explain that several types of raw material can be used to produce the product. The following ingredients were used:

soy meal: standard soy bean meal as now reduced but ground to a flour mesh (95 percent passes a screen of 200 mesh).

200/20: defatted soy flour with 20 protein dispersibility index (P.D.I.) and a granulation such that 95 percent passes through a screen of 200 mesh.

200/90: defatted soy flour with a P.D.I. of 85 and a granulation as above.

80/20: defatted soy flour with a P.D.I. of 30 and a granulation as that 95 passes through a screen of 80 mesh.

The enzyme modified proteinaceous product was prepared according to the following procedures:

A soy slurry was prepared in tap water of around 50° C. Soy meal or soy four was added under continuously stirring to the mixture till a homogeneous suspension was obtained with a dry solids varying from 25 to 28 percent. The pH of the soy slurry was corrected to pH 4.9 to 5.0 by addition of 10 percent hydrochloric acid. A viscosity reducing agent carbohydrase enzyme with 120 FBG/ml activity was added to degrade the non-starch polysaccharides, resulting in a reduced viscosity. The carbohydrase enzyme used was VISCOZYME 120L and was added in a dosage of 0.9 percent on the basis of a dry weight soy product. The soy product was kept under continuously stirring for two hours at 50° C.

The soy slurry was then heated using a jetcooking system, which includes the injection of direct steam of 12 bar followed by an intense mixing by an inliner mixer. The process was continuous and the slurry was kept at 125° C. to 135° C. for 5 minutes before cooling in a flashcooler to about 95° C. The slurry was then further cooled to 50° C. by using a tube cooler and pumped to a reaction vessel. The pH of the slurry was 4.9 to 5.0, and did not need to be corrected. The mixture of hydrolyzing enzymes containing an alpha-galactosidase, carbohydrase and protease were added in an amount of 1.62 percent on a dry weight soy product. The enzyme reaction was continuously stirred and at a temperature of about 46° C. to about 49° C. The hydrolyzing agent contained about 30,000 FBG units carbohydrase enzyme, about 96,000 GALU and about 25 AU protease units. The slurry was then spray dried using a spray drier with an atomizer wheel. The inlet temperature for the dryer varied between 190° C. and 210° C. The outlet temperature for the dryer varied between 80° C. and 90° C. The obtained product contained around 6 percent (5.5 to 6.3) moisture and 50 to 52 weight percent protein on a dry basis. The product was analyzed on simple sugars, trypsin inhibitor values and antigenicity as follows:

TABLE 4(i)

| | | Raw material | | | |
|---|---|---|---|---|---|
| raw materials | Trypsin inhibitor | Ant. | Raffinose | Stachyose | Saccharose |
| soy meal | 6.81 | +++ | 1.2 | 4.5 | 4.8 |
| 200/20 | 8.21 | +++ | 1.2 | 5.1 | 5.4 |
| 200/90 | 25 | +++ | 0.9 | 4.8 | 6.3 |
| 80/20 | 10.2 | +++ | 1.1 | 5.3 | 6.2 |

TABLE 4(ii)

| | | Enzyme Modified Soy | | | |
|---|---|---|---|---|---|
| raw materials | Trypsin inhibitor | Ant. | Raffinose | Stachyose | Saccharose |
| soy meal | 0.16 | — | <0.2 | <0.2 | <0.2 |
| 200/20 | 0.22 | — | <0.2 | <0.2 | <0.2 |
| 200/90 | −0.18 | — | <0.2 | <0.2 | <0.2 |

TABLE 4(ii)-continued

| raw materials | Trypsin inhibitor | Enzyme Modified Soy | | | |
|---|---|---|---|---|---|
| | | Ant. | Raffinose | Stachyose | Saccharose |
| 80/20 | 0.19 | — | <0.2 | <0.2 | <0.2 |

As can be seen in Example 4 in Tables 4(i) and 4(ii), the treated soy protein has substantially less raffinose, stachyose and trypsin inhibitor than the various raw materials. Also due to the process herein, all final products showed a negative antigenicity. It is clear from the table above that the type of raw material, the granulation and P.D.I. was of no direct influence on the levels of trypsin inhibitor, simple sugars and antigenicity of the final product.

Example 5

This example illustrates that there are several types of carbohydrase enzyme.

In this example, three types of carbohydrase enzymes were compared. All three are commercially available carbohydrases produced by fungi. Enzyme 1: VISCOZYME 120L from NOVO-Nordisk; Enzyme 2: ROHAMENT 7069 from Rohm; and Enzyme 3: ECONASE CE, which can be purchased from Alko. A soy slurry was prepared in tap water of around 50° C. Soy flour 200/20 (20 P.D.I. and with a granulation such that 95 percent passes a 200 mesh screen) was added under continuous stirring to the mixture till a homogeneous suspension was obtained with a dry solid varying from about 25 to about 26 percent. The pH of the soy slurry was corrected to pH 4.9-5.0 by addition of 10 percent hydrochloric acid. The carbohydrase enzyme was added and the slurry was pretreated for two hours under continuous stirring at 50° C. Dosage of the viscosity reducing enzyme for all three types of enzymes was 0.9 percent on dry weight basis of the product. The preparation process was as follows:

At regular time intervals the viscosity was measured using a Brookfield Spindle Viscosimeter at 42° C. As is clear from the Tables below, the viscosity of the slurry was reduced over the time when a carbohydrase enzyme was added to the soy slurry.

TABLE 5(i)

| Carbohydrase as a Viscosity Reducing Agent | | | |
|---|---|---|---|
| enzyme | Viscosity (cps) 0 hrs. | Viscosity (cps) 1.5 hrs. | Viscosity (cps) 3.5 hrs |
| no enzyme | 1340 | 1320 | 1350 |
| VISCOZYME 120L | 1340 | 1000 | 880 |
| ROHAMENT 7069 | 1340 | 960 | 410 |
| ECONASE CE | 1340 | 1050 | 910 |

TABLE 5(ii)

| enzyme | Viscosity (cps) 0 hrs. | Viscosity (cps) 1 hr. | Viscosity (cps) 2 hrs. |
|---|---|---|---|
| no enzyme | 1405 | 2350 | 2600 |
| VISCOZYME 120L | 1405 | 1415 | 960 |
| ROHAMENT 7069 | 1405 | 870 | 870 |
| ECONASE CE | 1405 | 1090 | 1060 |

As can be seen from Tables 5(i) and 5(ii), the carbohydrase reduces the viscosity of the soy slurry.

Example 6

About 230 to about 340 liters of soy slurry were prepared by adding, under continuous stirring, soy flour 200/90 to tap water (50° C.) till a homogeneous suspension was obtained, with a dry solid varying from about 25 to about 27.5 percent. The pH of the slurry was corrected to a pH of about 5.0 by adding 10 percent hydrochloric acid. The viscosity reducing agent carbohydrase agent was added in the range from 0.33 to about 0.87 percent on dry weight basis of the product. The viscosity reducing enzyme was added to hydrolyze the non-starch polysaccharides, which resulted in a lower viscosity before and after the heat treatment. The enzyme reaction proceeded for two hours under continuous stirring. The temperature of the slurry was kept between 42° C. and 48° C. by means of indirect heating. The slurry was then heated by passing it continuously through a jetcooker system which included the in-line mixer. The temperature during the heat treatment was 130° C.-135° C. and the slurry was kept at that temperature for 5-6 minutes before cooling in the flashcooler to about 90° C. The slurry was then further cooled in a tube cooler to about 50° C. and treated with the hydrolyzing agent in the form of a mixture containing a protease, an alpha-galactosidase and a carbohydrase.

Dosages of the hydrolyzing mixture varied between 1.19 to about 1.83 weight percent based on dry weight basis of the product. The hydrolyzing agents contained around 7.8 to about 33 AU units protease activity, 30,000 to about 48,000 FBG carbohydrase units and around 112,500 to about 160,000 GALU. The enzyme reaction proceeded for 4 hours under continuous stirring, while the temperature of the mixture was maintained between 42° C. and 51° C. by using indirect heating. The slurry was then spray dried using a spray dryer with inlet temperatures varying between 185° C. and 200° C. and outlet temperatures between 80° C. and 90° C. The obtained dry product was a free flowing powder with a moisture content varying between 4.0 and 6.0 weight percent. The protein content was between 50 and 52 weight percent on dry basis. The product showed an excellent mixability in lukewarm tap water (35° C.-40° C.) and a 20 weight percent solution remained stable for at least 4 hours. From each run, samples were analyzed for trypsin inhibitor factor, antigenicity and the simple sugars raffinose, stachyose and saccharose. During the process, the viscosities of the slurry were measured using a Brookfield Spindel Viscosimeter at 40° C.

In the following Tables 6a(i)-6b(ii), a review was done for 12 trials where the above procedures were followed. For each run, the soy flour 200/90 was used as raw material.

TABLE 6a(i)

| | 1 | 2 | 3 | 4 | 5 | 6 |
|---|---|---|---|---|---|---|
| kg soy flour | 108 | 108 | 80 | 76 | 76 | 76 |
| *% V.R.A. | 0.65 | 0.65 | 0.80 | 0.76 | 0.76 | 0.76 |
| Temp | 47 | 47 | 42-46 | 40-45 | 46 | 44 |
| Time (hrs) | 2 | 2 | 2 | 2 | 2 | 2 |
| Heat treatment | | | | | | |
| Temperature | 130 | 135-136 | 130-135 | 135 | 133 | 130-135 |
| Time (mins) | 5.5 | 5.5 | 5.5 | 5.5 | 5.5 | 5.5 |

TABLE 6a(i)-continued

|  | 1 | 2 | 3 | 4 | 5 | 6 |
|---|---|---|---|---|---|---|
| Enzyme reaction | | | | | | |
| Time | 4 | 4 | 4 | 4 | 4 | 4 |
| Temperature | 42-47 | 45 | 44 | 45 | 47 | 47 |
| % hydrolyzing mixture added | 1.55 | 1.61 | 1.76 | 1.7 | 1.83 | 1.72 |

*Where V.R.A. is viscosity reducing agent

TABLE 6a(ii)

|  | 1 | 2 | 3 | 4 | 5 | 6 |
|---|---|---|---|---|---|---|
| Viscosity (cps) | | | | | | |
| before heat treatment | 1228 | 910 | 1410 | 1440 | 1300 | 985 |
| after heat treatment | >8.000 | >8.000 | >8.000 | >8.000 | 4720 | >8.000 |
| after 1 hr | n.a. | 1180 | 1970 | n.a. | n.a. | 1495 |
| after 4 hrs | 1560 | 810 | 975 | 1120 | 544 | 884 |
| Dry solids | | | | | | |
| before heat treatment | 26.1 | 25.5 | 27.2 | 26.1 | 25.5 | 26.0 |
| after 4 hrs | 23.4 | 21.7 | 21.1 | 21.5 | 20.7 | 21.2 |
| pH | | | | | | |
| before heat treatment | 5.23 | 4.88 | 5.47 | 5.04 | 5.07 | 5.07 |
| before heat treatment | 5.30 | 4.98 | 5.18 | 5.19 | 4.96 | 5.24 |
| after 4 hrs | n.a. | 4.90 | 5.31 | 5.09 | n.a. | 5.12 |
| Dried proteinaceous product | | | | | | |
| T.I.F | 0.16 | 0.17 | 0.18 | 0.14 | 0.26 | 0.24 |
| Antigenicity | — | — | — | — | — | — |
| % Raffinose | <0.2 | <0.2 | <0.2 | <0.2 | <0.2 | <0.2 |
| % Stachyose | <0.2 | <0.2 | <0.2 | <0.2 | <0.2 | <0.2 |
| % Saccharose | <0.2 | <0.2 | <0.2 | <0.2 | <0.2 | <0.2 |

TABLE 6b(i)

|  | 7 | 8 | 9 | 10 | 11 | 12 |
|---|---|---|---|---|---|---|
| kg soy flour | 76 | 76 | 76 | 76 | 95 | 95 |
| *% V.R.A. | 0.76 | 0.76 | 0.76 | 0.76 | 0.33 | 0.33 |
| Temp | 45-50 | 50 | 45-50 | 45-50 | 45-50 | 45-50 |
| Time (hrs) | 2 | 2 | 2 | 2 | 2 | 2 |
| Heat treatment | | | | | | |
| Temperature | 132 | 132 | 133 | 132.5 | 132.5 | 132 |
| Time (mins) | 5 | 5 | 5 | 5 | 5 | 5 |
| Enzyme reaction | | | | | | |
| Time | 4 | 4 | 4 | 4 | 4 | 4 |
| Temperature | 42-50 | 47-51 | 47 | 45 | 47 | 47 |
| % hydrolyzing mixture added | 1.72 | 1.71 | 1.72 | 1.78 | 1.33 | 1.19 |

*Viscosity reducing agent

TABLE 6b(ii)

|  | 7 | 8 | 9 | 10 | 11 | 12 |
|---|---|---|---|---|---|---|
| Viscosity (cps) | | | | | | |
| before heat treatment | 1800 | 1300 | 1280 | 1264 | n.a. | n.a. |
| after heat treatment | <8000 | <8000 | <8000 | <8000 | <8000 | <8000 |
| after 1 hr | 5480 | 2910 | 3640 | 2140 | 4000 | 2400 |
| after 4 hrs | 1730 | 1590 | 1556 | 1269 | 1920 | 1034 |
| Dry solids | | | | | | |
| before heat treatment | 26.71 | 26.16 | 26.5 | 26.5 | 26.42 | 26.45 |
| after 4 hrs | 22.1 | 22.18 | 22 | 21.3 | 22.3 | 24.1 |
| pH | | | | | | |
| before heat treatment | 5.06 | 5 | 5.12 | 5.09 | 5.32 | 5.03 |
| before heat treatment | 5.27 | 5.27 | 5.23 | 5.07 | 5.2 | 5.2 |
| after 4 hrs | 5.02 | 5.07 | 5.09 | 4.97 | 5.01 | 4.81 |
| Dried proteinaceous product | | | | | | |
| T.I.F | 0.15 | 0.16 | 0.15 | 0.16 | 0.17 | 0.18 |
| Antigenicity | — | — | — | — | — | — |
| % Raffinose | <0.2 | <0.2 | <0.2 | <0.2 | <0.2 | <0.2 |
| % Stachyose | <0.2 | <0.2 | <0.2 | <0.2 | <0.2 | <0.2 |
| % Saccharose | <0.2 | <0.2 | <0.2 | <0.2 | <0.2 | <0.2 |

Example 7

A soy slurry was prepared by continuously adding soy flour 200/90 to lukewarm tap water (50° C). The slurry was continuously stirred till a homogeneous suspension was obtained. The pH of the slurry was corrected to around 5.0 with the addition of 10% hydrochloric acid. A viscosity reducing agent was added as a carbohydrase and antioxidant, and the antioxidant was sodium meta-bisulfite or mixtures of both were added as described in Table 7 a(i). The slurry was pretreated for two hours under continuous stirring. The temperature is maintained between 40° C. and 51° C. by using indirect heating.

The soy slurry was then heat-treated by passing the slurry continuously through a jetcooker (hydroheater M103MSX). Live steam 12.5 Bar was used to heat the slurry to around 150° C. Retention time at that temperature varied between 50 and 80 seconds before the slurry was cooled to 90° C.-95° C. in the flashcooler. The slurry was further cooled to around 50° C. by using a tube cooler. For the final enzyme treatment, a mixture containing hydrolyzing enzymes was added and the reaction did proceed for 4 hours under continuous stirring. The hydrolyzing agent was of the following mixture as described in Table 7 a(i). The temperature was maintained between 40° C. and 51° C. by using indirect heating. The slurry was then spray dried using a standard spray dryer with atomizer wheel. The air inlet temperature was between 190° C. and 200° C. The outlet temperature varied between 75° C. and 90° C. The final dry proteinaceous product was a free-flowing powder with a moisture content between 4 and 6 percent. The protein level varied between 50 and 52 percent. A 20 percent solution of the product in warm tapwater (35° C.) remained stable for at least 4 hours. During the process, the viscosity was measured by using a Brookfield Spindle Viscosimeter. The trypsin inhibitor factor, antigenicity and sugars were analyzed using the described methods.

TABLE 7a(i)

|  | 1 | 2 | 3 | 4 | 5 | 6 |
|---|---|---|---|---|---|---|
| kg soy flour | 18 | 18 | 18 | 22 | 18 | 24 |
| *% V.R.A. | 0.72 | 0 | 0.72 | 0.7 | 0.72 | 0.7 |
| % Antioxidant | 0.51 | 0.51 | 0 | 0.41 | 0 | 0.28 |
| Temp | 50 | 50 | 50 | 50 | 50 | 50 |
| Time (hrs) | 2 | 2 | 2 | 2 | 2 | 2 |
| Heat treatment | | | | | | |
| Temperature | 155 | 154 | 153 | 153 | 150 | 150 |
| Time (sec) | 60 | 60 | 80 | 60 | 80 | 70 |
| Enzyme reaction | | | | | | |
| Time | 4 | 4 | 4 | 4 | 4 | 4 |
| Temperature | 42–50 | 42–50 | 42–50 | 42–50 | 42–50 | 42–50 |
| % hydrolyzing mixture added | 1.53 | 1.75 | 1.57 | 1.53 | 1.24 | 1.87 |
| FBG/gr | 0.47 | 0.49 | 0.48 | 0.47 | 0.93 | 0.88 |
| AU/gr | 0 | 0 | 0 | 0 | 0.0002 | 0 |
| GALU/gr | 2.65 | 2.8 | 2.73 | 2.66 | 0 | 0.99 |

FBG: carbohydrase enzyme activities per gram dry product
AU: protease activities per gram dry product
GALU: alpha-galactosidase activities per gram dry product
*Viscosity reducing agent

TABLE 7a(ii)

|  | 1 | 2 | 3 | 4 | 5 | 6 |
|---|---|---|---|---|---|---|
| Viscosity (cps) | | | | | | |
| before heat treatment | 1950 | 4270 | 1650 | 2850 | 1700 | 4500 |
| after heat treatment | >8000 | >8000 | >8000 | >8000 | >8000 | >8000 |
| after 4 hrs | 1020 | 1300 | 720 | 940 | 360 | 1370 |
| Dry solids | | | | | | |
| before heat treatment | 20.49 | 20.95 | 19.97 | 21.5 | 19.32 | 30.1 |
| after 4 hrs | 20.66 | 20.02 | 19.55 | 21.45 | 18.9 | 23.58 |
| pH | | | | | | |
| before heat treatment | 5.06 | 6.35 | 5.2 | 5.16 | 5.15 | 5.13 |
| before heat treatment | 4.82 | 5.3 | 4.9 | 5.2 | 4.82 | 5.2 |
| after 4 hrs | 4.72 | 5.17 | 4.92 | 5.2 | 4.82 | 5 |
| Dried proteinaceous product | | | | | | |
| T.I.F | 0.17 | 0.74 | 0.31 | 0.16 | 0.49 | 0.19 |
| Antigenicity | — | — | — | — | — | — |
| % Raffinose | <0.2 | <0.2 | <0.2 | <0.2 | <0.2 | <0.2 |
| % Stachyose | <0.2 | <0.2 | <0.2 | <0.2 | <0.2 | <0.2 |
| % Saccharose | <0.2 | <0.2 | <0.2 | <0.2 | <0.2 | <0.2 |

What is claimed is:

1. A method of making a proteinaceous product by treating sources of vegetable protein and carbohydrates that contain non-starch polysaccharides to improve palatability, digestibility, and minimize proteinaceous antinutritional factors and antigenicity factors, which comprises:
   a) preparing an aqueous slurry of vegetable proteins and carbohydrates;
   b) adjusting the pH of the slurry between about 3.5 and about 6;
   c) pretreating the slurry to reduce the viscosity below about 4000 cps by reacting a viscosity reducing agent with the slurry;
   d) heating the slurry to a temperature between about 85° C. and about 155° C. for a period of time to substantially minimize proteinaceous antinutritional factors and antigenicity factors;
   e) cooling the slurry so that a hydrolyzing agent that is added in step (f) is not inactivated;
   f) hydrolyzing the slurry with a hydrolyzing agent from a source of alpha-galactosidase.

2. The process for making a proteinaceous product as in claim 1 wherein the pH of the slurry is adjusted with an acid selected from the group consisting of hydrochloric acid, phosphoric acid, an organic acid, and mixtures thereof.

3. The process for making a proteinaceous product as in claim 2 wherein the acid is a mixture of hydrochloric acid and citric acid.

4. The process for making a proteinaceous product as in claim 1 wherein the slurry has a dry solids content of about 15 to about 35 weight percent.

5. The process for making a proteinaceous product as in claim 1 wherein the viscosity reducing agent is selected from the group consisting of a carbohydrase enzyme, an antioxidant, and mixtures thereof.

6. The process for making a proteinaceous product as in claim 5 wherein the viscosity reducing agent is a mixture of a carbohydrase enzyme, an antioxidant, and further contains a protease enzyme.

7. The process for making a proteinaceous product as in claim 6 wherein the viscosity reducing agent further contains an amino acid.

8. The process for making a proteinaceous product as in claim 5 wherein the carbohydrase is an enzyme complex containing cellulase, hemicellulase, pectinase, xylanase, invertase, beta-glucanase, cellobiase or arabinase.

9. The process for making a proteinaceous product as in claim 8 wherein the viscosity reducing agent is a mixture of carbohydrase enzyme and antioxidant.

10. The process for making a proteinaceous product as in claim 9 wherein the antioxidant is sodium metabisulfite.

11. The process for making a proteinaceous product as in claim 10 wherein, before drying, hydrogen peroxide is added to the slurry.

12. The process for making a proteinaceous product as in claim 9 wherein the mixture is about 0.02 to about 1.5 weight percent carbohydrase enzyme and about 0.05 to about 1.2 weight percent antioxidant.

13. The process for making a proteinaceous product as in claim 12 wherein the mixture is about 0.1 to about 0.8 weight percent carbohydrase enzyme and about 0.1 to about 0.6 weight percent antioxidant.

14. The process for making a proteinaceous product as in claim 8 wherein the carbohydrase enzyme has an activity of at least 120 FBF units/ml where the complex has an activity of about 150 to about 800 cellulase, about 140 to about 800 xylanase, about 50 to about 10,000 pectinase, about 100 to about 600 hemicellulase, about 300 to about 1000 pentosanase, about 1300 to about 7000 beta-glucanase, about 1 to about 10 cellobiase, all in micromol. product/minute/gram substrate units.

15. The process for making a proteinaceous product as in claim 7 wherein an amino acid cysteine is added to the viscosity reducing agent.

16. The process for making a proteinaceous product as in claim 15 wherein cysteine is used in an amount of about 200 to about 800 ppm.

17. The process for making a proteinaceous product as in claim 10 wherein, after pretreatment with the viscosity reducing agent, the viscosity of the slurry is about 1000 to about 4000 cps.

18. The process for making a proteinaceous product as in claim 17 wherein the viscosity of the pretreated slurry is not greater than about 2000 cps.

19. The process for making a proteinaceous product as in claim 1 wherein the slurry in step (d) is heated between about 100° C. to about 135° C.

20. The process for making a proteinaceous product as in claim 19 wherein the slurry in step (d) is heated between about 105° C. to about 120° C.

21. The process for making a proteinaceous product as in claim 20 wherein the slurry is heated using a jet-cooker line.

22. The process for making a proteinaceous product as in claim 20 wherein the slurry is mixed after heating in a high speed mixer.

23. The process for making a proteinaceous product as in claim 1 wherein the alpha-galactosidase is used in an amount of about 0.2 to about 1.3 weight percent.

24. The process for making a proteinaceous product of claim 1 wherein the hydrolyzing agent further contains a carbohydrase enzyme and the hydrolyzed slurry is spray dried.

25. The process for making a proteinaceous product as in claim 1 wherein the hydrolyzing agent further contains a carbohydrase enzyme.

26. The process for making a proteinaceous product as in claim 1 wherein the hydrolyzing agent further contains protease enzyme.

27. The process for making a proteinaceous product as in claim 26 wherein the hydrolyzing agent is about 0.2 to about 1.3 weight percent alpha-galactosidase with an activity of 250 GALU grams, about 0.1 to about 1.0 weight percent of carbohydrase enzyme with an activity of 120 FBG/ml, about 0.5 to about 2.4 weight percent protease with an activity of 0.5 AU/gram.

28. The process for making a proteinaceous product as in claim 25 wherein the carbohydrase is an enzyme complex containing cellulase, hemicellulase, pectinase, xylanase, invertase, beta-glucanase, cellobiase and arabinase.

29. The process for making a proteinaceous product as in claim 28 wherein the carbohydrase enzyme has an enzyme activity of about 150 to about 800 cellulase, about 140 to about 800 xylanase, about 50 to about 10,000 pectinase, about 100 to about 600 hemicelllulase, about 300 to about 1000 pentosanase, about 1500 to about 7000 beta-glucanase, about 1 to about 10 cellobiase, all in microl. product/minute/gram substrate units.

30. The process for making a proteinaceous product as in claim 26 wherein the enzyme mixture contains about 0.0005 to about 0.005 AU protease activity, about 0.1 to about 1.0 FBG carbohydrase activity and about 0.35 to about 2.5 GALU alpha-galactosidase activity to be added to one gram dry product.

31. The process for making a proteinaceous product as in claim 30 wherein the enzyme mixture contains 0.00125 to about 0.004 AU protease activity, about 0.2 to about 0.85 FBG carbohydrase activity, and about 1.0 to about 2.5 GALU alpha-galactosidase activity to be added to one gram dry product.

32. The process for making a proteinaceous product as in claim 25 wherein the carbohydrase is made by a fungi selected from the group consisting of *Aspergillus* strain, *Trichoderma* strain, *Penicillium* strain, and mixtures thereof.

33. The process for making a proteinaceous product as in claim 32 wherein the fungi from the *Aspergillus* strain is *Aspergillus niger* or *Aspergillus oryzae*.

34. The proteinaceous product made by the process as in claim 32 wherein the fungi from the *Trichoderma* strain is *Trichoderma longibrahiatum*.

35. The proteinaceous product made by the process as in claim 32 wherein the fungi from the Penicillium strain is *Penicillium emersonii* or *Penicillium funiculosum*.

36. The proteinaceous product made by the process as in claim 26 wherein the protease is made by a fungi from the *Aspergillus* or *Bacillus* strain.

37. The proteinaceous product made by the process as in claim 36 wherein the fungi from the *Aspergillus* strain is *Aspergillus oryzae*; and the fungi from the *Bacillus* strain is *Bacillus lichenformis* or *Bacillus subtilus*.

38. The proteinaceous product made by the process as in claim 1 wherein the alpha-galactosidase is made by a fungi from *Aspergillus* strain; *Bacillus* strain, or *Monascus* strain.

39. The proteinaceous product made by the process as in claim 38 wherein the fungi from the *Aspergillus* strain is *Aspergillus niger* or *Aspergillus oryzae*; from the *Bacillus* strain is *Bacillus stearothermophilus*: or from the *Monascus* strain is *Monascus pilosus*.

40. The proteinaceous product made by the process as in claim 27 wherein the hydrolyzing agent is used in an amount of about 0.5 to about 2.4 weight percent, where the alpha-galactosidase has an activity of 250 GAL units/gram, carbohydrase enzyme has an activity of 120 FBG/ml; protease has an activity of 0.5 AU/gram.

41. The proteinaceous product of claim 1 comprising about 48 to about 54 percent protein, about 10 to about 22 percent simple sugars, where the sugar contains about 4 to about 9 percent glucose and galactase and about 3 to about 6 percent fructose.

42. The proteinaceous product of claim 1 wherein the level of saccharose, stachyose and raffinose are individually lower than about 0.5 percent based on the weight of the proteinaceous product.

43. The proteinaceous product as in claim 1 wherein the product is used in food for human consumption.

44. The proteinaceous product as in claim 1 wherein the product is used in a calf milk replacement product, pet food, pig starter, fish or feed.

45. The proteinaceous product of claim 1 wherein said proteinaceous product is a milk replacement product which comprises about 5 to about 30 weight percent proteinaceous product; about 30 to about 50 weight percent whey protein and about 5 to about 20 weight percent skim milk.

46. The proteinaceous product of claim 45 wherein said milk replacement product contains about 19 weight percent proteinaceous product; about 42 weight percent whey protein products; about 11 weight percent skim milk and about 20 weight percent fat.

47. The milk replacement product of claim 46 that further contains about 1 to about 10 weight percent starch or pig gelatinized starch.

48. A process as in claim 1 wherein the slurry contains soy flour, water and an acid to adjust the pH of the slurry between about 3.5 and about 6.

49. A process as in claim 48 which further comprises (g) drying the proteinaceous material by spray drying to form a proteinaceous product, where the hydrolyzing agent used is a mixture of alpha galactosidase, carbohydrase and protease.

50. The proteinaceous product of claim 1 wherein the amount of trypsin is less than about 1.0 mg inhibited trypsin per gram of product.

* * * * *

UNITED STATES PATENT AND TRADEMARK OFFICE
CERTIFICATE OF CORRECTION

PATENT NO. : 5,100,679　　　　　　　　　　　　Page 1 of 3
DATED : March 31, 1992
INVENTOR(S) : Delrue It is certified that error appears in the above-identified patent and that said Letters Patent is hereby corrected as shown below:

ON THE TITLE PAGE

Item [56], References Cited - Other Publications, in the publication of "Abstract of U.S. Pat. No. 4,944,952" change "et a" to --et al.--.

Column 1, line 31, after "stimulated" change "a" to --an--.

Column 2, line 23, change "4,483874" to --4,483,874--.

Column 4, line 59, change "Asperoillus" to --Aspergillus--.

Column 5, line 49, delete the bold face type of "50".

Column 6, line 15, at the end of the line, after "to" insert --about--.

Column 6, line 25, change "ca" to --can--.

Column 6, line 28, change "VISCOXYME" to --VISCOZYME--.

Column 6, line 37, change "units/mol" to --units/ml--.

Column 6, line 44, change "the" to --The--.

Column 6, line 59, change "alpha-galactosidase" to --alpha-galactosidases--.

UNITED STATES PATENT AND TRADEMARK OFFICE
CERTIFICATE OF CORRECTION

PATENT NO. : 5,100,679

DATED : March 31, 1992

INVENTOR(S) : Delrue

It is certified that error appears in the above-identified patent and that said Letters Patent is hereby corrected as shown below:

Column 6, line 65, change "stearothermphilus" to --stearothermophilus--.

Column 6, line 68, change "Mot" to --Most, and after "is", second occurrence, insert --a--.

Column 7, line 3, change "hydrolyeses" to --hydrolyses--.

Column 7, line 10, change "abut" to --about--.

Column 10, line 2, change "anti-nutritional" to --antinutritional--.

Column 11, line 35, under column C2 for SOYCOMILL, change "11.0" to --11.00--.

Column 11, line 59, change "mil" to --milk--.

Column 12, line 33, under the heading "TABLE 2(iv)", insert the title of the table, --STABILITY--.

Column 12, line 53, change "weighting" to --weighing-- and change "45" to --46--.

Column 13, line 28, change "scourging" to --scouring--.

Column 14, line 1, change "reduced" to --produced--.

Column 14, line 15, change "four" to --flour--.

UNITED STATES PATENT AND TRADEMARK OFFICE
CERTIFICATE OF CORRECTION

PATENT NO. : 5,100,679

DATED : March 31, 1992

INVENTOR(S) : Delrue

It is certified that error appears in the above-identified patent and that said Letters Patent is hereby corrected as shown below:

```
    Column 15, line 39, after "product." move "The" to the
left margin on the next line.

Column 18, line 23, change "T.I.F" to --T.I.F.--.

Column 19, line 15, change "(sec)" to --(sec.)--.

Column 19, line 24, change "0.0002" to --0.002--.

Column 19, line 53, change "T.I.F" to --T.I.F.--.

Column 22, line 13, italicize "Penicillium".

Column 22, line 31, after "stearothermophilus" change
the colon to a semicolon.

Column 22, line 68, change "pig gelatinized" to --
pregelatinized--.
```

Signed and Sealed this

Tenth Day of August, 1993

Attest:

MICHAEL K. KIRK

*Attesting Officer*   *Acting Commissioner of Patents and Trademarks*